United States Patent
Abe

(10) Patent No.: US 9,189,569 B2
(45) Date of Patent: Nov. 17, 2015

(54) NON-TRANSITORY COMPUTER READABLE MEDIUM, MEDICAL RECORD SEARCH APPARATUS, AND MEDICAL RECORD SEARCH METHOD

(71) Applicant: FUJI XEROX CO., LTD., Minato-ku, Tokyo (JP)

(72) Inventor: Masaki Abe, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 271 days.

(21) Appl. No.: 13/862,635

(22) Filed: Apr. 15, 2013

(65) Prior Publication Data

US 2014/0143232 A1 May 22, 2014

(30) Foreign Application Priority Data

Nov. 21, 2012 (JP) ................................. 2012-254908

(51) Int. Cl.
*G06F 17/30* (2006.01)
*G06F 19/00* (2011.01)

(52) U.S. Cl.
CPC .......... *G06F 17/30991* (2013.01); *G06F 19/32* (2013.01); *G06F 17/30247* (2013.01)

(58) Field of Classification Search
CPC .............................................. G06F 17/30247
See application file for complete search history.

(56) References Cited

U.S. PATENT DOCUMENTS

| | | | |
|---|---|---|---|
| 2005/0060195 A1* | 3/2005 | Bessette et al. | 705/2 |
| 2008/0021288 A1* | 1/2008 | Bowman et al. | 600/300 |
| 2008/0037852 A1* | 2/2008 | Zhou et al. | 382/132 |
| 2009/0112627 A1* | 4/2009 | Berkman et al. | 705/3 |
| 2010/0082610 A1* | 4/2010 | Anick et al. | 707/723 |
| 2010/0232661 A1* | 9/2010 | Hisanaga et al. | 382/128 |
| 2012/0066197 A1* | 3/2012 | Rana et al. | 707/706 |
| 2012/0173285 A1* | 7/2012 | Muthukrishnan | 705/3 |
| 2013/0096937 A1* | 4/2013 | Campbell et al. | 705/2 |

FOREIGN PATENT DOCUMENTS

| | | |
|---|---|---|
| JP | 6-292656 A | 10/1994 |
| JP | 2000-123098 A | 4/2000 |
| JP | 2004-287732 A | 10/2004 |
| JP | 2011-22704 A | 2/2011 |
| JP | 2012-45419 A | 3/2012 |

\* cited by examiner

*Primary Examiner* — Mohammad S Rostami
(74) *Attorney, Agent, or Firm* — Sughrue Mion, PLLC

(57) ABSTRACT

A non-transitory computer readable medium stores a program causing a computer to execute a process. The process includes searching a document memory, the document memory storing electronic documents of medical records of patients in association with document types of the electronic documents, for electronic documents associated with a patient specified by a user from among the patients; referring to group definition information that defines document groups and grouping the electronic documents obtained in the searching so as to create the document groups; and generating data of a search result display screen in which an icon associated with a corresponding one of the document groups created as a result of the grouping is arranged at a position of a schema, the position corresponding to a site of a human body associated with the document group.

6 Claims, 11 Drawing Sheets

FIG. 2

| PATIENT ID | DOCUMENT ID | DOCUMENT NAME | CREATOR ID | SITE CODE | DOCUMENT TYPE CODE |
|---|---|---|---|---|---|
| A0001 | DOC001 | LETTER OF INTRODUCTION | D0100 | | C0001 |
| A0001 | DOC003 | EXAMINATION RECORD | D0200 | W0001 | C0002 |
| A0002 | DOC102 | RADIOGRAPH | D0100 | W0002 | C0003 |
| A0003 | DOC219 | LETTER OF INTRODUCTION | D0100 | | C0001 |

FIG. 3

| PATIENT ID | PATIENT NAME | DOCTOR-IN-CHARGE ID | DEPARTMENT |
|---|---|---|---|
| A0001 | PATIENT A | D0100 | INTERNAL MEDICINE, SURGERY, OTOLARYNGOLOGY |
| A0002 | PATIENT B | D0100 | SURGERY, OPHTHALMOLOGY |
| A0003 | PATIENT C | D0200 | INTERNAL MEDICINE |
| ⋮ | ⋮ | | |

FIG. 4

| SITE CODE | SITE NAME |
|---|---|
| W0001 | HEAD |
| W0002 | HEART |
| W0003 | LUNG |

FIG. 5

| DOCUMENT TYPE CODE | DOCUMENT TYPE NAME |
|---|---|
| C0001 | LETTER OF INTRODUCTION |
| C0002 | EXAMINATION REPORT |
| C0003 | CHEST RADIOGRAPH |
| C0004 | CONSENT DOCUMENT |

FIG. 6

| DOCUMENT GROUP ID | DOCUMENT GROUP NAME | MEMBER DOCUMENT TYPE CODE | REPRESENTATIVE SITE CODE | IMPORTANCE |
|---|---|---|---|---|
| G0001 | FIRST VISIT | C0001, C0002 | | 1 |
| G0002 | CHEST EXAMINATION | C0002, C0003 | W0003 | 2 |
| G0003 | ENDOSCOPIC EXAMINATION | C0002, C0004 | W0006 | 3 |

FIG. 7

| DOCUMENT ID | CONCURRENTLY VIEWED DOCUMENT ID | NUMBER OF TIMES OF CONCURRENT VIEWING |
|---|---|---|
| DOC001 | DOC002 | 12 |
| DOC001 | DOC003 | 7 |
| ⋮ | ⋮ | ⋮ |

NON-TRANSITORY COMPUTER READABLE MEDIUM, MEDICAL RECORD SEARCH APPARATUS, AND MEDICAL RECORD SEARCH METHOD

CROSS-REFERENCE TO RELATED APPLICATIONS

This application is based on and claims priority under 35 USC 119 from Japanese Patent Application No. 2012-254908 filed Nov. 21, 2012.

BACKGROUND (i) Technical Field

The present invention relates to a non-transitory computer readable medium, a medical record search apparatus, and a medical record search method.

(ii) Related Art

Paper documents of various types or formats, such as medical charts, letters of introduction, and various examination records, and data of various types or formats, such as radiographs and moving or still images resulting from endoscopic examinations, are stored as consultation and treatment records at medical institutions, such as hospitals.

In recent years, systems have been developed which make a database of various types of documents and data regarding medical records to centrally manage the various types of documents and data. Systems of this type search for documents or the like that satisfy a search condition specified by the user (such as a doctor who refers to medical records) and present a list of the retrieved documents or the like to the user. This list shows, for example, for each of the retrieved documents, attribute information such as the document name that represents the document (which is associated with actual data of the document or the like), the registration date and time and the registrant of the document, and the name of the doctor in charge. The user selects a document or the like that they wish to read from the list so that the actual data of the document is loaded and displayed on the screen.

Such a display method using a list requires the user to recognize individual search results from text information, such as the document name or the attribute. Thus, finding a desired document is not necessarily easy.

SUMMARY

According to an aspect of the invention, there is provided a non-transitory computer readable medium storing a program causing a computer to execute a process. The process includes searching a document memory, the document memory storing electronic documents of medical records of patients in association with document types of the electronic documents, for electronic documents associated with a patient specified by a user from among the patients; referring to group definition information that defines document groups and grouping the electronic documents obtained in the searching so as to create the document groups; and generating data of a search result display screen in which an icon associated with a corresponding one of the document groups created as a result of the grouping is arranged at a position of a schema, the position corresponding to a site of a human body associated with the document group.

BRIEF DESCRIPTION OF THE DRAWINGS

An exemplary embodiment of the present invention will be described in detail based on the following figures, wherein:

FIG. 2 illustrates an example of management data of individual medical record documents stored in a medical record document database;

FIG. 3 illustrates an example of data stored in a patient database;

FIG. 4 illustrates an example of definition information of site codes;

FIG. 5 illustrates an example of definition information of document type codes;

FIG. 6 illustrates an example of the content of data stored in a group definition database;

FIG. 7 illustrates an example of concurrent access history information;

DETAILED DESCRIPTION

An exemplary embodiment of the present invention will be described below with reference to the accompanying drawings.

Figure 1:
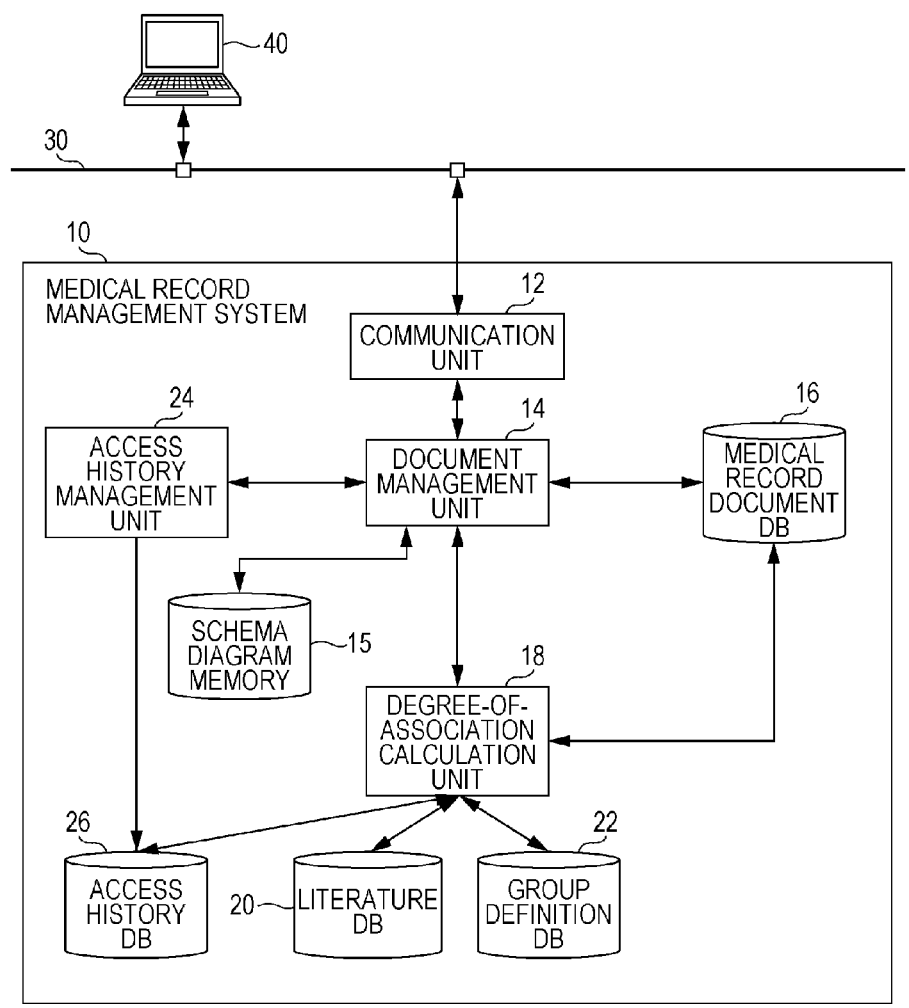
FIG. 1 illustrates an example of a system according to an exemplary embodiment.

A medical record management system 10 according to this exemplary embodiment illustrated in FIG. 1 is installed in a network 30, for example, a local area network (LAN) or the Internet. The user (for example, a doctor) operates a terminal 40 to access the medical record management system 10 via the network 30 and receives a service from the medical record management system 10.

The medical record management system 10 includes a communication unit 12, a document management unit 14, and a medical record document database (DB) 16. The communication unit 12 controls data communication performed via the network 30. The document management unit 14 is a system that manages the medical record document DB 16. The document management unit 14 searches the medical record document DB 16 for documents in response to a search request received from the terminal 40, and provides a search result to the terminal 40. As a user interface (UI) for displaying this search result, the document management unit 14 provides a schema-based screen in which the retrieved documents are arranged at corresponding positions of a schema.

A schema is a drawing of the human body or a part of the human body written on medical charts by doctors and is used, for example, for recording the position and state of the affected part or the like. In this exemplary embodiment, each retrieved document is displayed at a corresponding position of a schema. In this way, the user is notified of which site of the patient body that each document is related to.

Data of schemas used to display the search result is stored in a schema memory 15. Examples of the stored schemas include a schema of the whole human body. In addition to this schema, schemas of body parts, such as the upper body, the lower body, the head, the chest, and the abdomen, may be registered in the schema memory 15.

Medical record documents of individual patients are registered in the medical record document DB 16. The medical record documents registered in the medical record document DB 16 are subjected to a search in this exemplary embodiment.

Medical record documents are electronic documents, which are created in relation to consultation and treatment of patients and stored as records. Medical record documents include a variety of kinds of documents, for example, medical charts, examination reports, letters of introduction (from other medical institutions), consent documents (for surgery or the like), radiographs, and moving images recorded by the endoscope. The data formats of medical record documents are not limited to a particular format and may be any formats, for example, document files created by a document creation application, scanned document files including images obtained by scanning paper documents, still image data, moving image data, and multimedia data.

Medical record documents of each patient are subjected to a search in this exemplary embodiment. Literatures, such as medical papers, stored in a literature DB 20 to be described later are used as reference information for searching medical record documents but are not directly subjected to a search in this exemplary embodiment. In the description below, medical record documents stored in the medical record document DB 16 are simply referred to as "documents" occasionally, whereas medical papers or the like stored in the literature DB 20 are simply referred to as "literatures" occasionally.

FIG. 2 illustrates an example of management data of individual medical record documents stored in the medical record document DB 16. One row of a table illustrated in FIG. 2 corresponds to management data of one medical record document. In this example, management data of one medical record document includes information about the patient identification (ID), the document ID, the document name, the creator ID, the site code, and the document type code.

The patient ID is identification information that uniquely identifies a patient associated with this medical record document. Medical institutions that use this system have a patient database for managing patients (not illustrated). The patient ID is identification information of each patient used in this patient database. FIG. 3 illustrates an example of the content of data stored in the patient database. In the example of FIG. 3, data of one patient includes information about the patient ID, the name of the patient (the patient name), the doctor-in-charge ID that uniquely identifies the doctor in charge, and a list of departments for the patient.

The document ID is identification information that uniquely identifies this medical record document. Actual data of each medical record document is stored in the medical record document DB 16 in association with this document ID. The document name is a title assigned to the medical record document by the user. The creator ID is identification information that uniquely identifies a user who has created this medical record document.

The site code is a code representing a site associated with this medical record document among sites of the body. Each site of the body is assigned a unique code in advance and a code for a site associated with the medical record document is selected from among these codes. Some medical record documents are not associated with a specific site, and no site code is set for such medical record documents. FIG. 4 illustrates an example of definition information of site codes. For example, in the example of FIG. 4, a site code "W0001" is assigned to the "head" and a site code "W0002" is assigned to the "heart". Although illustration is omitted, each part, such as the "head" or the "heart", is associated with a position of a schema of the human body.

The document type code is a code representing the type of the medical record document, for example, the medical chart, the examination report, the letter of introduction, or the radiograph. FIG. 5 illustrates an example of definition information of document type codes. In this example, for example, a code "C0001" represents a document type "letter of introduction" and a code "C0002" represents a document type "examination report".

The definition information illustrated in FIGS. 4 and 5 may be stored at a location accessible from the medical record management system 10.

The items of the management data illustrated in FIG. 2 are merely examples and the management data may include other items. For example, the management data may include information about the date and time when the medical record document was registered in the medical record document DB 16 and the date and time when the medical record document was updated. Also, consultation identification information may be automatically assigned at the time of the first visit, and the consultation identification information may be recorded in the management data of medical record documents used when follow-up consultations or medical procedures, such as examination, medication, and surgery, are performed after the first visit. In this way, a group of documents created for one symptom from the first visit to the recovery may be managed by using the same consultation identification information. Also, information about a symptom of a patient associated with medical record documents (including information about the affected site and the diagnosis or symptom) may be entered in the medical record management system 10 and identification information of the symptom may be registered in the management data of the medical record documents. The management data need not include all items mentioned above.

The document management unit 14 uses a degree-of-association calculation unit 18 in order to search for related documents.

The degree-of-association calculation unit 18 calculates a degree of association between a document specified by the user (hereinafter, referred to as a "reference document") and each medical record document in order to allow for retrieval of medical record documents related to the reference document. In this exemplary embodiment, the degree-of-association calculation unit 18 calculates the degree of association in terms of three points: the document content, the document group, and the concurrent access. Specifically, the degree-of-association calculation unit 18 refers to the literature DB 20 in order to calculate the degree of association in terms of the document content, refers to a group definition DB 22 in order to calculate the degree of association in terms of the document group, and refers to an access history DB 26 in order to calculate the degree of association in terms of the concurrent access.

Electronic data of medical information literatures, such as medical papers, that are not directly related to individual patients is registered in the literature DB 20. In this exemplary embodiment, by way of example, a keyword (referred to as a first keyword) is extracted from the reference document when medical record documents having the content related to the reference document are searched for. The literature DB 20 is searched for literatures containing the first keyword. A keyword contained in the retrieved literatures is extracted as a second keyword. Then, the medical record document DB 16 is searched for medical record documents containing the first and second keywords many times. As described above, in this exemplary embodiment, a search is performed using not only the first keyword contained in the reference document but also the second keyword that appears together with the first keyword in the medical information literatures. In this way, the number of medical record documents that fail to be retrieved is reduced. Any available keyword extraction technique may be used to extract keywords from the reference document and the related literatures stored in the literature DB 20.

The group definition DB 22 stores definition information of document groups. A document group is constituted by medical record documents created or used for one medical event or for one series of medical procedures performed for one symptom.

Here, the medical event is units of medical procedures that are regarded as one set. Examples of the medical event include one consultation, one examination, one surgery, and one hospital stay. It is not rare that types of documents created or used for a medical event are fixed depending on the kind of the medical event, such as two types of documents, namely, the letter of introduction and the examination report, being used for a medical event "first visit" and two types of documents, namely, the examination report and the chest radiograph, being created for a medical event "chest examination", for example. In this exemplary embodiment, a set of medical record documents created or used for one medical event in this manner is treated as one document group.

It is often convenient if documents used in a series of medical procedures performed for one symptom between the first visit to the recovery are made viewable collectively. Thus, documents for a series of medical procedures performed from the first visit to the recovery may be treated as one document group.

FIG. 6 illustrates an example of the content of data stored in the group definition DB 22. One row of a table illustrated in FIG. 6 corresponds to definition information of one document group. Definition information of each document group includes information about the group definition ID, the group definition name, the member document type code, the representative site code, and the importance. The group definition ID is identification information that uniquely identifies the group definition. The group definition name is a name representing the group definition and, in the illustrated example, is the name of the medical event associated with the group definition. The member document type code is a list of document type codes of medical record documents belonging to a document group based on the group definition.

The representative site code is a code representing a site of the body associated with the group definition. For example, because the X-ray examination is performed on lungs in a medical event "chest examination", the representative site code of the group definition associated with this medical event is "W0003", which represents "lungs". In some cases, consultation and examination may be performed on multiple sites in one medical event and medical record documents are individually created. However, even in such cases, a main site subjected to the medical procedure in the medical event is often fixed. Thus, the main site subjected to the medical procedure is set as the "representative site" and a code representing the "representative site" may be set as the "representative site code". Also, in some medical events, such as the "first visit", the representative site subjected to the medical procedure is not specified. In such a case, the field of the representative site code for the document group corresponding to such a medical event is kept empty.

The importance is a value indicating a degree of importance of the document group and is used in calculation of the degree of association (which will be described in detail later).

A group of medical record documents used in a series of medical procedures performed for one symptom from the first visit to the recovery is identifiable from the consultation identification information contained in the management data of the individual medical record documents.

The access history DB 26 is a database that records a history of accesses to (viewing of) each medical record document stored in the medical record document DB 16 made by each user. Each access history record includes information about when which user accessed which medical record document (for example, a set of the access date and time, the user ID of the user who made the access, and the document ID of the accessed medical record document). An access history management unit 24 detects an access to each medical record document stored in the medical record document DB 16 made by the user via the document management unit 14, and records such access history information in the access history DB 26.

Also, information about a medical record document accessed (viewed) by the user together (concurrently) with this medical record document may be recorded in the access history DB 26. That is, in the case where the user also views another medical record document when they view a certain medical record document using this system, information indicating that the former and the latter are viewed together is recorded in the access history DB 26. Here, the state in which multiple documents are viewed or accessed "together" (or "concurrently") is not limited to a state in which the multiple documents are displayed on the screen at the same time. For example, multiple documents viewed by the user within one session that may be sectioned in accordance with a predetermined rule, such as multiple documents viewed within a predetermined length of time or multiple documents selected and viewed from the list of search results obtained from one search, may be recognized as documents accessed "together".

FIG. 7 illustrates an example of the content of concurrent access history data stored in the access history DB 26. In this example, for each pair of document IDs of medical record documents viewed together, the number of times the pair has been viewed together is recorded in the access history DB 26. For example, in the case where three documents A, B, and C are viewed together, the number of times a pair of A and B has been viewed concurrently, the number of times a pair of B and C has been viewed concurrently, and the number of times a pair of C and A has been viewed concurrently are individually incremented by 1. The number of times the pair has been viewed concurrently is regarded as an index that represents the degree of association between medical record documents constituting the pair.

Instead of creating or updating the concurrent access history illustrated in FIG. 7 every time medical record documents are accessed, the concurrent access history may be dynamically created from basic access history information (for example, the date and time, the user ID, and a set of the document IDs) in a search process (to be described later).

In this exemplary embodiment, a schema is used in a search result UI screen generated by the document management unit 14.

Figure 8:
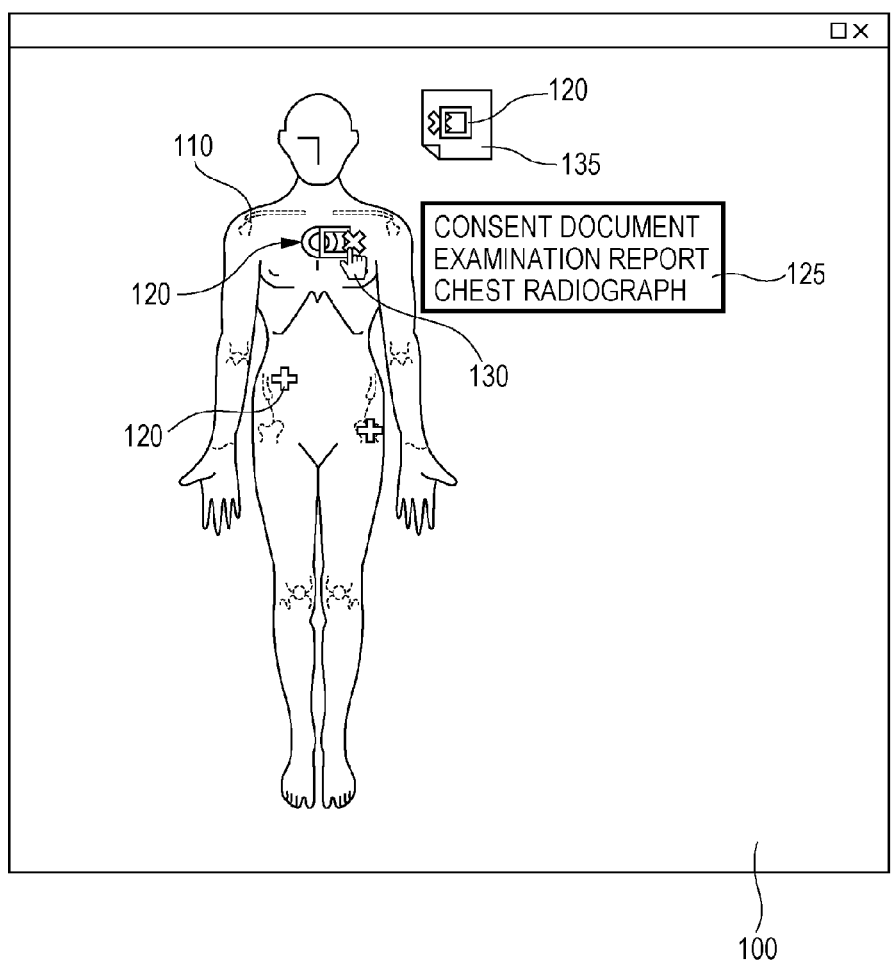
FIG. 8 illustrates an example of a search result display screen.

FIG. 8 illustrates an example of a search result display screen 100. In this example, the search result display screen 100 shows a schema 110 of the whole human body. Document icons 120 representing corresponding retrieved medical record documents are arranged on the schema 110. Here, each document icon 120 is arranged at a position corresponding to a site represented by the site code associated with this medical record document stored in the medical record document DB 16. The medical record management system 10 has information about a position (site) of the schema associated with each site code. Based on this information, the document management unit 14 arranges each document icon 120 at a position of the schema 110 corresponding to the site. Each document icon 120 arranged on the schema 110 is associated with the document ID of the corresponding medical record document. This allows the user to access the corresponding document by selecting the document icon 120 using a user interface mechanism (for example, a mouse or touch panel) of the medical record management system 10. For example, upon the user placing a mouse cursor 130 over the document icon 120, the document name of the document corresponding to the document icon 120 is displayed (here, attributes other than the document name may be displayed). Also, for example, upon the user performing a predetermined mouse operation, such as double clicking, with the mouse cursor 130 being placed over the document icon 120, a file of the medical record document corresponding to the document icon 120 is opened and the content of the medical record document is displayed on the screen.

In the case where the search result includes multiple medical record documents associated with the same site, the document icons 120 for the individual medical record documents are displayed so as to be superposed with each other at the same position. At this time, display is performed to indicate that the multiple document icons 120 are superposed with each other at the position. In an example, the positions of the document icons 120 are slightly shifted from each other so that an icon located on the background side is not completely hidden by an icon located on the foreground side. In the illustrated example, three documents associated with the site "chest" are retrieved and the document icons 120 for the three documents are displayed so as to be superposed with each other at the position of the chest. In this example, upon the user placing the mouse cursor 130 over the position of the chest where the document icons 120 are superposed with each other, a list 125 of three document names corresponding to the three document icons 120 arranged at the chest is displayed (here, other document attributes may be displayed together). Upon the user placing the mouse cursor 130 over a document name contained in the list 125 and then performs a predetermined operation, such as double clicking, a file of the document corresponding to the document name is opened.

Some documents contained in the search result may be associated with no site code (for example, the document ID="D00001" of FIG. 2). The document icons 120 for such documents are displayed at a special display area 135 that is provided outside the schema in the search result display screen 100.

The manner (for example, the shape, the color, or a combination thereof) in which the document icons 120 are displayed on the search result display screen 100 may be changed in accordance with document attributes of individual documents stored in the medical record document DB 16. In the display example of FIG. 8, the shape of the document icon 120 representing a document is changed in accordance with the document type represented by the document type code of the document. The document type is merely an example, and obviously the display manner of the document icon 120 may be changed in accordance with another document attribute. Alternatively, the display manner of the document icon 120 may be changed in accordance with a combination of multiple document attributes, such as the shape of the document icon 120 being changed in accordance with the document type and the color thereof being changed in accordance with the registration date.

Figure 9:
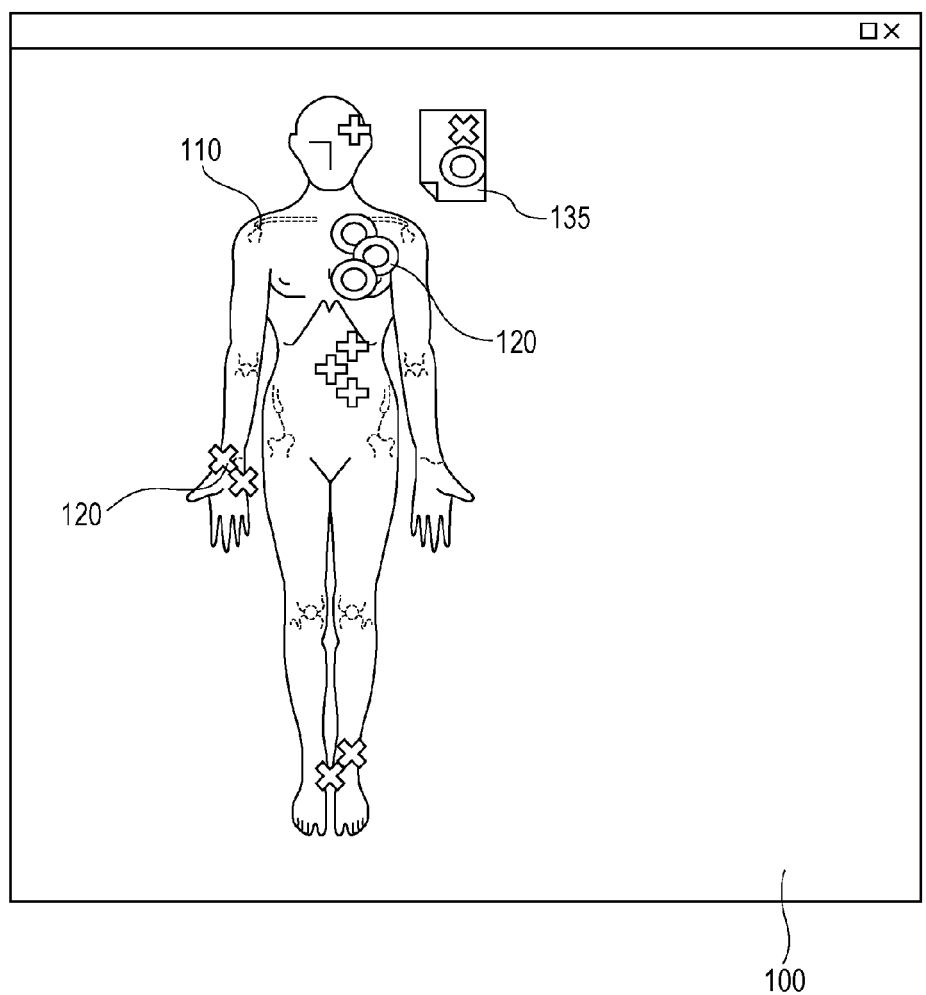
FIG. 9 illustrates another example of the search result display screen.

FIG. 9 illustrates another example of the search result display screen 100. In this example, the display manner of the document icon 120 (the shape of the document icon 120 in the illustrated example) is changed in accordance with the degree of association between this document and the reference document, instead of the document attribute of this document.

Figure 10:
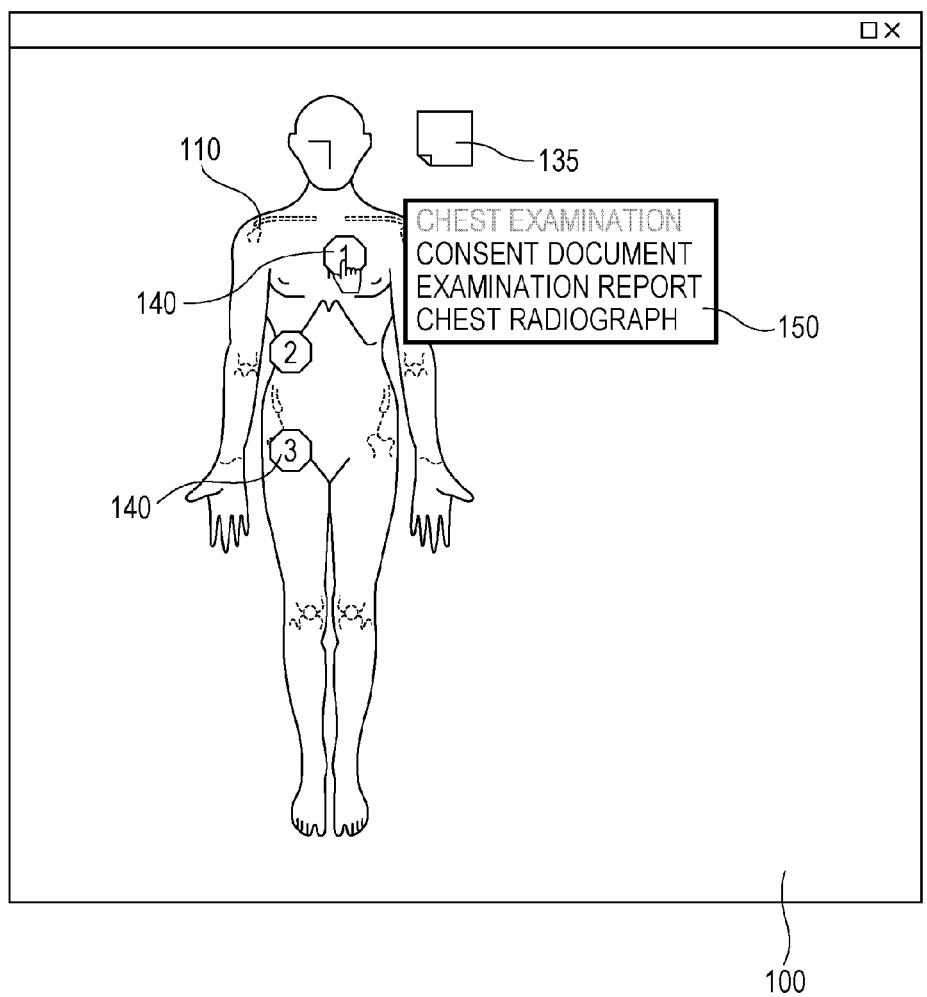
FIG. 10 illustrates still another example of the search result display screen.

FIG. 10 illustrates still another example of the search result display screen 100. The example screens illustrated in FIGS. 8 and 9 display icons for individual documents, whereas the example screen of FIG. 10 displays icons for individual document groups. In this example, for each document group created in accordance with a corresponding document group definition registered in the group definition DB 22, a group icon 140 representing the document group is arranged at a position of the schema 110 corresponding to the representative site code of the document group. In the example of FIG. 10, document groups for the chest, the right flank, the right thigh are retrieved and document groups that are not associated with any sites (to be displayed at the special display area 135) are not retrieved. Upon the user placing the mouse cursor 130 over the group icon 140, group information 150 corresponding to the group icon 140 is displayed. The group information 150 includes information about the document group name (this may be the same as the group definition name of the group definition from which the document group is created, such as "chest examination" in the illustrated example, and see also FIG. 6) of the document group corresponding to the group icon 140 and a list of document names of documents belonging to the document group. Upon the user placing of the mouse cursor 130 over each document name contained in the group information 150, attribute information of the document may be displayed in a popup manner. Alternatively, a site represented by the site code associated with a document over which the mouse cursor 130 is placed may be emphasized (for example, a document icon is temporarily displayed at the position) on the schema 110. Alternatively, in the case of a hierarchical grouping method which permits a document group to include another document group (such as a document group for one symptom from the first visit to the recovery including a group of documents used in a chest examination for the symptom), the group information 150 associated with an icon of the highest layer group displayed on the schema 110 may contain a group name of another document group included in the document group represented by the icon. Upon the user placing the mouse cursor 130 over this group name, a list of documents included in this group may be displayed in a popup manner.

Although not illustrated in the example of FIG. 10, multiple retrieved document groups are possibly associated with the same site of the body. In such a case, as in the example of FIG. 8, the multiple group icons 140 are displayed so as to be superposed with each other at a position corresponding to the site.

Upon the user placing the mouse cursor 130 over the position where the multiple group icons 140 are superposed with each other, a list of document group names corresponding to these group icons 140 are displayed in one example as in the example of FIG. 8. Then, upon the user placing the mouse cursor 130 over any of document group names included in the list, a list of document names of documents belonging to the document group is displayed. Upon the user performing an operation, such as double clicking, on any of the document names included in this list, a document corresponding to the document name is opened.

Figure 11:
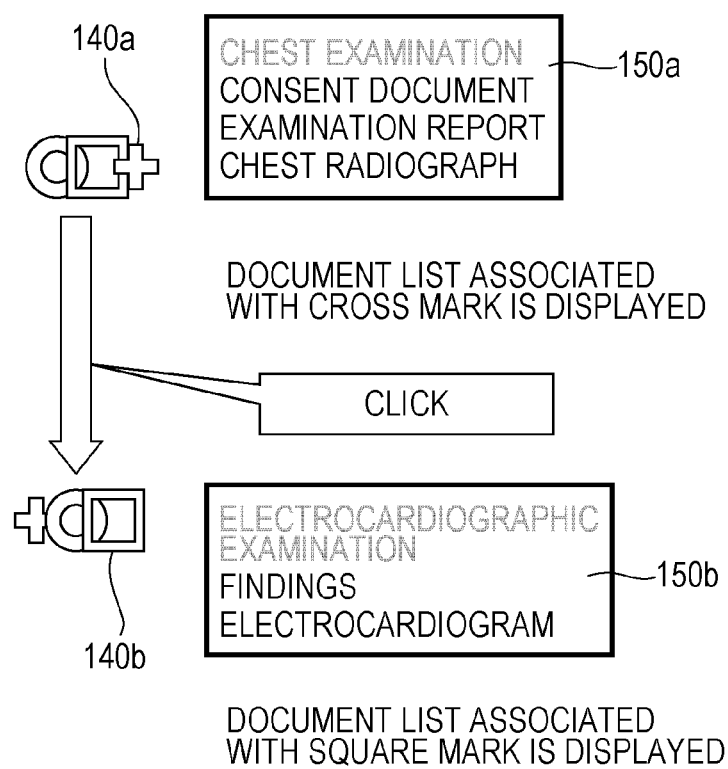
FIG. 11 describes switching performed in the case where multiple icons are superposed with each other at the same position.

A display method of displaying a list of document group names corresponding to the group icons 140 located at a position where the mouse cursor 130 is placed in this manner is merely an example. Instead of this, a list of document names of documents belonging to a document group corresponding to the group icon 140 located at the top in the superposition order may be displayed among the multiple group icons 140 associated with the position where the mouse cursor 130 is placed. The superposition order of the group icons 140 is updated in such a manner that, for example, in response to a predetermined operation, such as single clicking, the group icon 140 at the top is moved to the bottom and the order of the other group icons 140 is advanced by one position. Then, a list of document names of documents belonging to a document group corresponding to the group icon 140 located at the top after the update is displayed. For example, in an example illustrated in FIG. 11, group information 150a representing documents belonging to a group "chest examination" corresponding to a cross-mark group icon 140a located at the top is displayed first. Upon the user performing a single click operation using the mouse in this state, a group icon 140b (represented by a square mark) of a group "electrocardiographic examination" that has been at the second position from the top moves to the top. Consequently, group information 150b representing documents belonging to the group "electrocardiographic examination" is displayed.

The search result display screen 100 of various types illustrated in FIGS. 8 to 10 are switched between in response to a selection operation performed by the user. Alternatively, a hitherto used screen of a retrieved document list that does not use a schema may be displayed concurrently side by side with the screen using a schema, or the hitherto used screen and the screen using a schema may be displayed in a switching manner.

The examples of FIGS. 8 to 10 illustrate the front view of the whole human body as a schema displayed on the search result display screen 100 but the front view of the whole human body is merely an example. Alternatively, schemas of the front view and the back view of the whole human body may be registered in the schema memory 15, and a document associated with a site on the back side of the human body may be displayed at a corresponding position of the back-view schema in the search result display screen 100. Alternatively, schemas for individual parts, such as the head, the chest, and the abdomen, may be prepared in addition to the whole body schemas. For example, upon the user specifying a partial schema, the schema displayed in the search result display screen 100 may be switched from the whole body schema into the specified partial schema and icons for retrieved documents or document groups may be displayed at corresponding positions of the partial schema.

Referring now to FIGS. 12 to 15, an example of a procedure of a search and grouping of search results performed by the document management unit 14 will be described. This process is an example of a process performed in the case where retrieved documents that are grouped into document groups are displayed as the group icons 140 and those that are not grouped are displayed as the document icons 120 on the schema 110.

This procedure starts upon the user (for example, a doctor) inputting a related document search instruction to the document management unit 14 from a menu accompanying a display window while viewing a medical record document (for example, a medical chart) of a certain patient displayed on the display window of the display of the terminal 40. The medical record document that is being displayed on the display window at this time serves as the reference document used in the related document search. The document management unit 14 acquires the document ID of the displayed reference document and also acquires the patient ID associated with the document ID from the medical record document DB 16 (S10). The document management unit 14 searches medical record documents of the patient associated with the acquired patient ID for related documents that are related to the medical record document corresponding to the acquired document ID. In order to perform this search, the document management unit 14 supplies the document ID and the patient ID to the degree-of-association calculation unit 18 and requests the degree-of-association calculation unit 18 to create a related document list. The document management unit 14 then acquires the related document list determined by the degree-of-association calculation unit 18 (S12).

Figure 14:
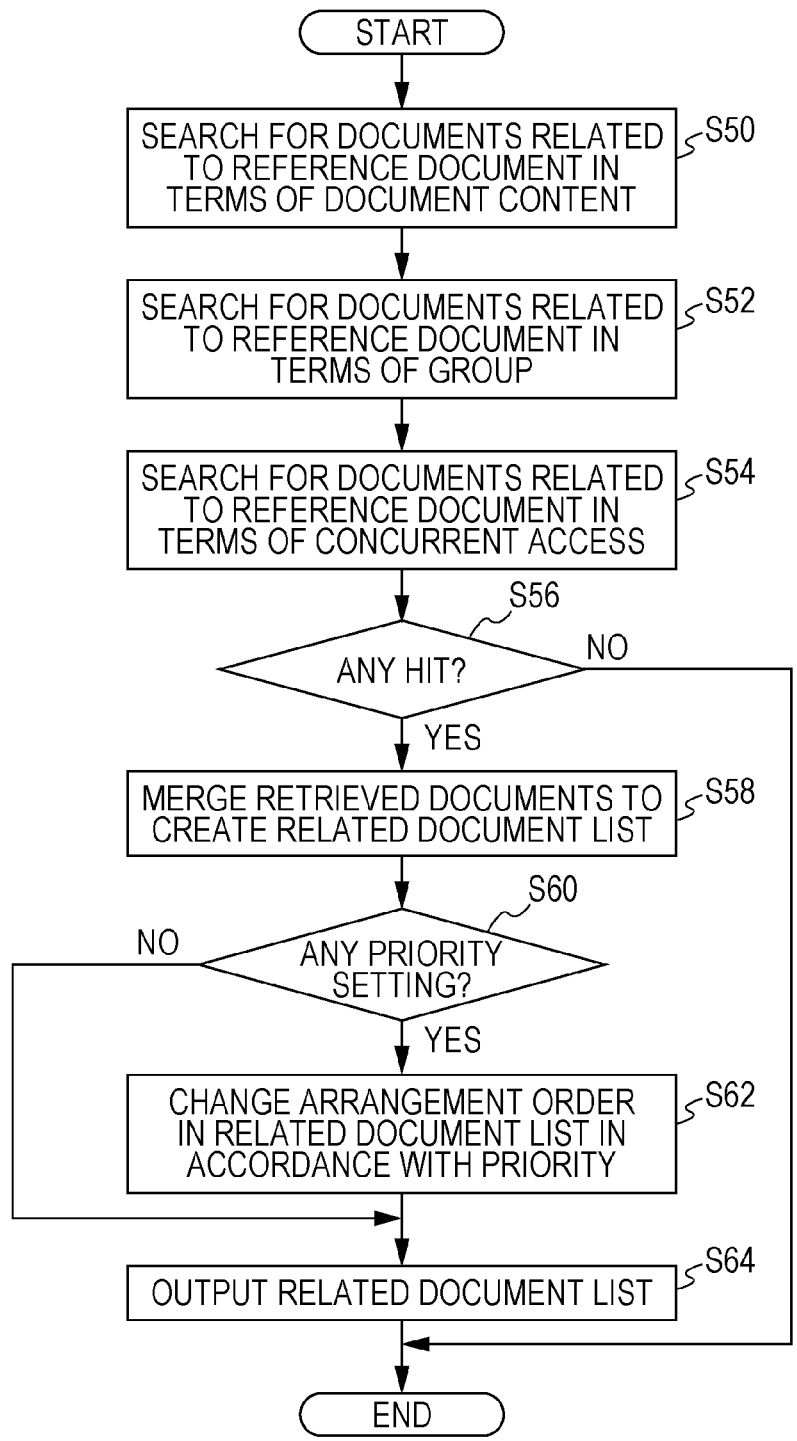
FIG. 14 illustrates an example of a procedure of a related document search process performed by a degree-of-association calculation unit.
Figure 15:
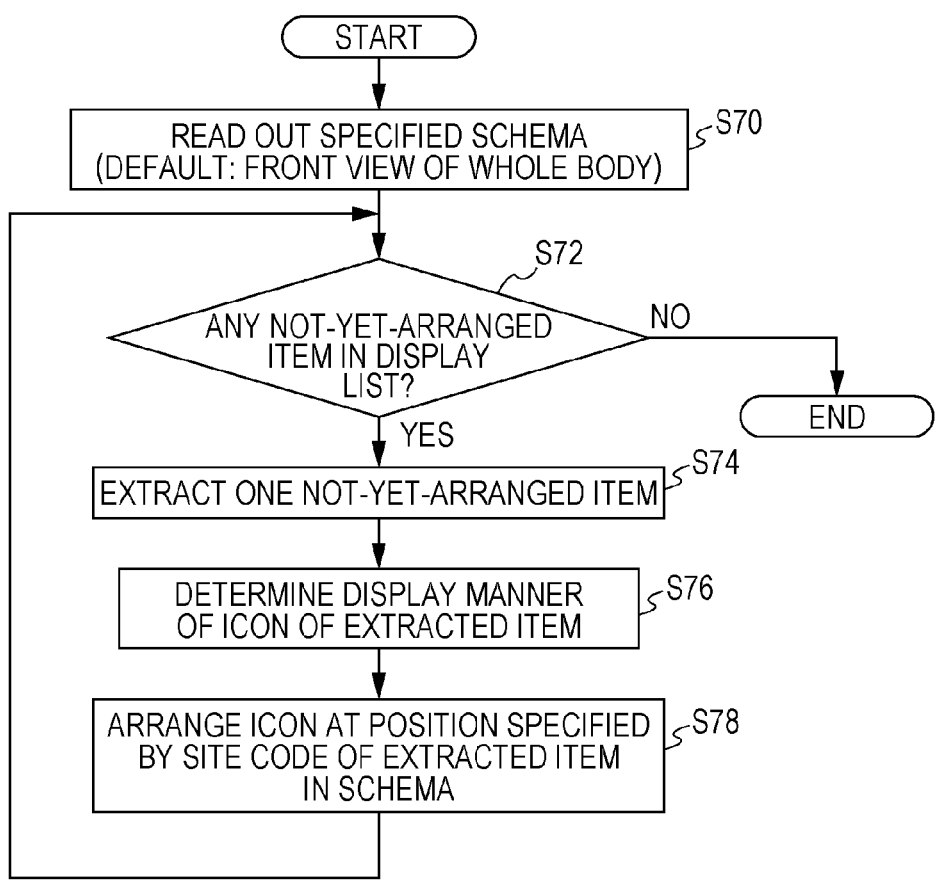
FIG. 15 illustrates an example of a procedure of creating the search result display screen performed by the document management unit.

Referring to FIG. 14, an example of a procedure of the process performed by the degree-of-association calculation unit 18 in response to the request made in S12 will be described. In this procedure, the degree-of-association calculation unit 18 extracts documents associated with the patient ID received along with the request from the medical record document DB 16. From among the extracted documents, the degree-of-association calculation unit 18 searches for related documents that are related to the reference document specified by the document ID received along with the request in terms of three points: the document content, the document group, and the concurrent access (S50, S52, and S54).

In S50, the degree-of-association calculation unit 18 calculates, for each of the extracted documents, a degree of association between the document and the reference document in terms of the document content. The degree of association in terms of the document content is a value that represents how much the document content of each document is related to (resembles) the document content of the reference document. Examples of the method for determining the degree of association in terms of the document content include a method using keywords. In this method, the degree of association between each of the extracted documents and the reference document is determined on the basis of how many keywords related to keywords (for example, terms for diagnosis or symptoms) contained in the reference document are contained in the document. Here, in addition to keywords contained in the reference document, namely, first keywords, keywords that appear along with the first keywords in medical literatures accumulated in the literature DB 20, namely, second keywords, may be taken into account. Specifically, for each of the extracted documents, the degree-of-association calculation unit 18 determines the number of first keywords and the number of second keywords contained in the document, and then determines the degree of association between the document and the reference document (in terms of the document content) in accordance with the numbers of first and second keywords. For example, the sum of the number of first keywords and the number of second keywords contained in the document may be used as the degree of association or the sum may be normalized using the total number of words contained in the document and the normalized sum may be used as the degree of association. Also, for each of the extracted documents associated with the patient, the degree-of-association between the document and a query containing the first and second keywords may be determined using a term frequency-inverse document frequency (tf-idf) weight that is commonly used in the document search field. Any available keyword extraction technique may be used to extract keywords from the reference document and each literature stored in the literature DB 20.

The above-described method for determining the degree of association in terms of the document content is merely an example. In addition to the above method, various methods for determining the degree of association or the degree of similarity are available in the document search field or the like, and any of the available methods may be used in S50.

The degree-of-association calculation unit 18 extracts each document whose the degree of association between this document and the reference document determined in terms of the document content in this manner is greater than or equal to a predetermined threshold. The documents extracted in this manner are documents related to the reference document in terms of the document content.

In S52, the degree-of-association calculation unit 18 calculates, for each of the documents associated with the patient, a degree-of-association between the document and the reference document in terms of the document group. The degree of association in terms of the document group is a value that becomes larger as the possibility of the document belonging to the same group as the reference document becomes higher.

In one example, in order to determine this degree of association, the degree-of-association calculation unit 18 determines the document type code of the reference document from the medical record document DB 16, and then determines group definitions each including the determined document type code as its "member document type code" (see FIG. 6) from the group definition DB 22. For each of the determined group definitions, the degree-of-association calculation unit 18 extracts documents associated with each document type code included as the member document type code in the group definition, from the medical record document DB 16. Then, for each of the extracted documents, the degree-of-association calculation unit 18 determines the degree of association between the document and the reference document (in terms of the document group) on the basis of the value of "importance" of the group definition associated with the document type code of the document. Here, in the case where the document type code of the extracted document is associated with multiple group definitions, the degree of association is calculated on the basis of the sum of the importance values of these group definitions. The sum of the importance values may be used as the degree of association or the degree of association may be determined using a function that outputs a larger value for a larger sum of the importance values.

Specifically, in the case where the document type of the reference document is "examination report" (the document type code thereof is "C0002", see FIG. 5), three group definitions "first visit", "chest examination", and "endoscopic examination" are extracted as group definitions including the document type of the reference document, from the group definition DB 22 storing information illustrated in FIG. 6. For example, a document having the document type code "C0004", among documents of the patient stored in the medical record document DB 16, satisfies the document type contained in the group definition "endoscopic examination" among these three group definitions. Thus, the degree of association between this document and the reference document is a value based on the importance "3" of the group definition "endoscopic examination". Now, suppose that the documents of the patient include a document having the document type that belongs to both group definitions "chest examination" and "first visit", which is different from the example of FIG. 6. The degree of association of this document is a value based on the sum of the importance "2" of the group definition "chest examination" and the importance "1" of the group definition "first visit".

The example of FIG. 6 indicates that the larger the importance value, the higher the importance of the group definition.

Also, in FIG. 6, an examination report of a chest examination and an examination report of an endoscopic examination are assigned the same document type. Thus, for example, in the case where an examination report of an endoscopic examination is set as the reference document, a chest radiograph and a chest examination report belonging to a document group "chest examination" are also treated as documents related to the reference document at a degree based on the importance "2". However, in some cases, it may be desired that only documents related to the endoscopic examination be searched for from the reference document regarding the endoscopic examination. In order to meet such a need, for example, more detailed document types than those illustrated in FIG. 6 may be set in such a manner that for example, different document types are assigned to the examination report of the chest examination and the examination report of the endoscopic examination.

The degree-of-association calculation unit 18 extracts each document whose the degree of association between this document and the reference document determined in terms of the document group in this way is greater than or equal to a predetermined threshold (this threshold may be set independently of the threshold used when related documents are determined in terms of the document content). The documents extracted in this manner are documents related to the reference document in terms of the document group.

In S54, the degree-of-association calculation unit 18 calculates, for each of the documents associated with the patient, a degree of association between the document and the reference document in terms of concurrent access. The degree of association in terms of concurrent access is a value that becomes larger as the number of documents that have been "accessed concurrently (at the same time)" with the reference document increases. The meaning of the term "accessed concurrently (at the same time)" is explained before. The degree-of-association calculation unit 18 refers to the access history DB 26 (see FIG. 7) and determines the document IDs of documents that have been accessed (viewed) concurrently with the reference document and the number of times of concurrent access (viewing). Then, the degree-of-association calculation unit 18 determines the degree of association between each of the concurrently accessed documents and the reference document on the basis of the number of times of concurrent access. The number of times of concurrent access may be used as the degree of association or a function that outputs a larger degree of association for a larger number of times of concurrent access may be used.

The degree-of-association calculation unit 18 extracts each document whose the degree of association between this document and the reference document determined in terms of concurrent access in this way is greater than or equal to a predetermined threshold (this threshold may be set independently of the thresholds used when related documents are determined in terms of the document content and the document group). The documents extracted in this manner are documents related to the reference document in terms of concurrent access.

The processing of S50, S52, and S54 described above need not be performed in the illustrated order and may be performed in any order.

As a result of the above process, related documents that are related to the reference document in terms of the document content, document group, and concurrent access are extracted.

The above-described method for determining related documents in terms of the three points is merely an example. One of the three points may be used alone or one of combinations each constituted by two points among the three points may be used. Alternatively, various methods for determining a degree of association between documents by using the content or attribute of the documents are available. Any of these available methods may be used in a search for related documents performed in this exemplary embodiment.

After performing searches for related documents related to the reference document in S50 to S54, the degree-of-association calculation unit 18 determines whether or not one or more related documents are found as a result of these searches (S56). If no related document is found, processing of S58 to S64 described below is skipped. The degree-of-association calculation unit 18 returns a response indicating that no related document is found to the document management unit 14 and terminates the process.

Upon determining that one or more related documents are found in S56, the degree-of-association calculation unit 18 merges document IDs obtained as a result of the searches performed in terms of the three points and creates a related document list (S58). The degree-of-association calculation unit 18 then determines whether or not priorities are specified among the three points (S60). If priorities are specified, the degree-of-association calculation unit 18 changes an order in which the document IDs are arranged in the related document list, in accordance with the specification (S62). For example, in the case where the priorities are specified in such a manner that the highest priority is assigned to the document content, the second highest priority is assigned to the concurrent access, and the third highest priority is assigned to the document group, the degree-of-association calculation unit 18 first sorts the document IDs contained in the related document list in the descending order of the degree of association in terms of the document content. The priority may be registered in the medical record management system 10 beforehand by the user as setting information, for example. Then, the degree-of association calculation unit 18 sorts document IDs having the same score in this sorted result in the descending order of the degree of association in terms of concurrent access, and thereafter sorts document IDs having the same score in this sorted result in the descending order of the degree of association in terms of the document group. The degree-of-association calculation unit 18 then outputs the related document list obtained as a result of such sorting processing to the document management unit 14 (S64).

In the example of FIG. 14, related documents are searched for in terms of the three points individually and the search results are then sorted in accordance with the priorities assigned to the three points. However, this is merely an example. Instead of this, for example, the degree of association between each document stored in the medical record document DB 16 and the reference document may be calculated for each of the three points in the above-described manner. Thereafter, the three degrees of association may be integrated to determine an overall degree of association. The search ranks of the documents may be determined in accordance with the overall degree of association (such as by sorting search results in the descending order of the overall degree of association). The overall degree of association may be determined, for example, using a method in which a weighted addition is performed, using weights assigned to the individual points, on the degrees of association determined in terms of the three points.

Figure 12:
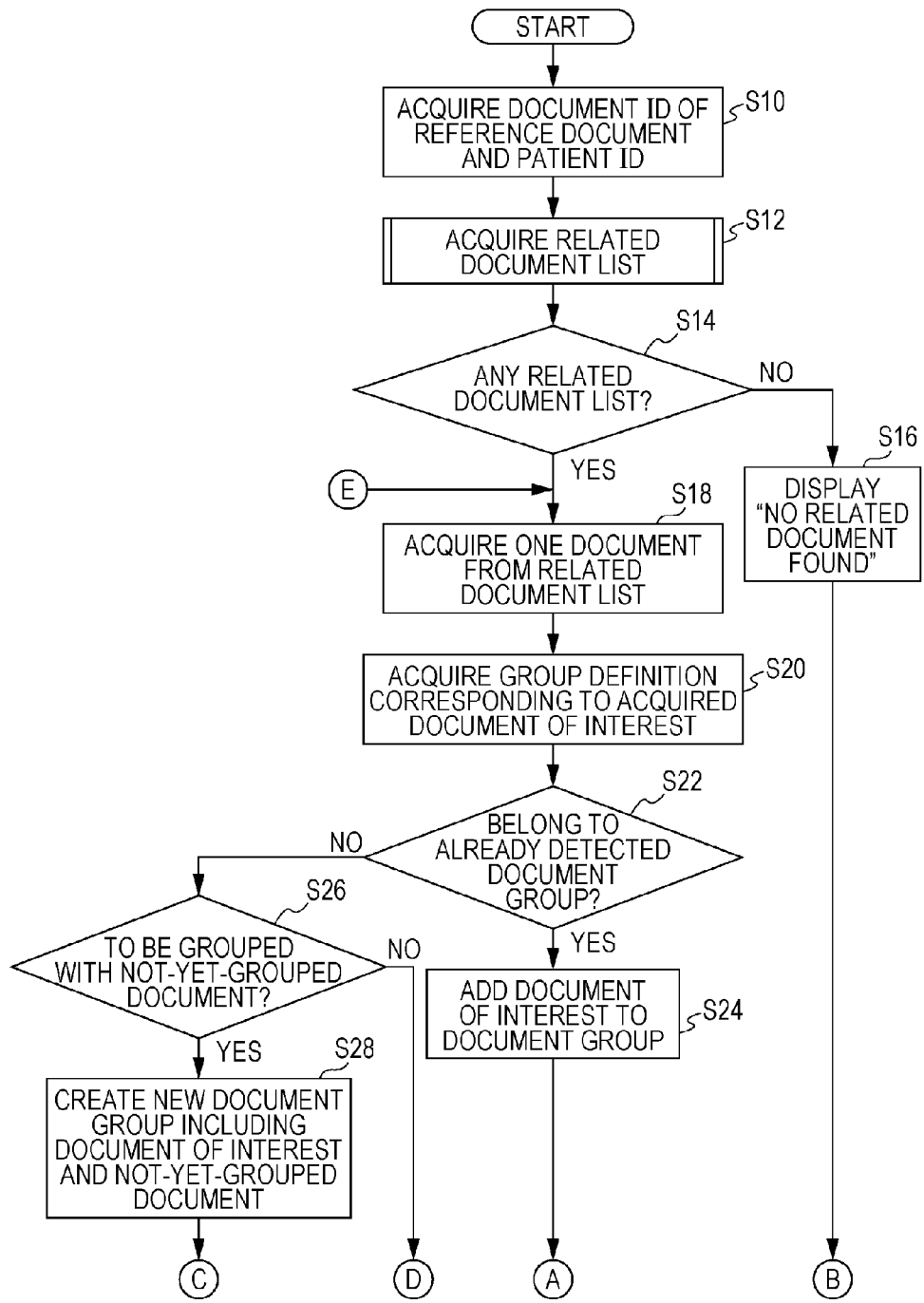
FIG. 12 illustrates an example of a procedure of a search and grouping of search results performed by a document management unit.

Now, the description returns to FIG. 12, and the document management unit 14 having received the search result from the degree-of-association calculation unit 18 determines whether or not the search result includes the related document list (S14). If the related document list is not included, the document management unit 14 displays a message indicating that no related document is found on the screen (S16) and terminates the process. If the related document list is included, the document management unit 14 extracts one document (specifically, the document ID) from the related document list (S18). Here, the document extracted in S18 is called a document of interest. Then, the document management unit 14 determines the document type code of the document of interest from the medical record document DB 16, and acquires a group definition that includes this document type code as its member document type code from the group definition DB 22 (S20). In S20, two or more group definitions associated with the document of interest are possibly found. The document management unit 14 then checks whether or not a document group to which the document of interest belongs exists among document groups that have been already created for the documents contained in the related document list (S22). In S22, a document group, among the already created document groups, that satisfies any one of the group definitions acquired in S20 and that includes a member document whose registration date differs from that of the document of interest by a predetermined threshold or less (for example, two days) is determined as the document group to which the document of interest belongs. For example, in the case where a patient receives a stomach endoscopic examination a few years after they received a stomach endoscopic examination, documents of the same combination of document types are created for the preceding examination and the following examination. In the case where a medical procedure of the same type (such as the same examination or the same surgery) is performed multiple times at a certain time interval in this manner (that is, in the case where multiple medical events for the medical procedure of the same content are performed), documents having the same format are created for individual medical procedures (medical events) and are recorded. In such a case, documents assigned close registration dates are grouped in this example in order to sort documents for the individual medical procedures into different document groups. Documents for individual medical procedures may be grouped using a document attribute other than the registration date.

In the case where document groups need not be sorted separately for individual medical events and documents of multiple medical events for the medical procedure of the same content (for example, multiple stomach endoscopic examinations) may be collectively grouped, narrowing based on the registration date of each document may be omitted.

If a document group to which the document of interest belongs is found in S22, the document management unit 14 adds the document of interest to the document list of the document group (S24). The process proceeds to S38 of FIG. 13 from S24, and the document management unit 14 determines whether or not processing of all documents contained in the related document list is finished.

On the other hand, if a document group to which the document of interest belongs is not found in S22, the document management unit 14 determines whether or not the document of interest and any of not-yet-grouped documents are to be grouped (S26). A not-yet-grouped document is a document that has been extracted from the related document list in S18 and whose document group has not yet been determined at the time of extraction of the document. It is determined whether or not a not-yet-grouped document and a document extracted from the related document list are to be grouped in the following processing loop (S26).

In S26, the following processing is performed for each not-yet-grouped document held by the document management unit 14. Specifically, if group definitions associated with the document of interest (namely, group definitions including the document type code of the document of interest as their member document type code) and group definitions associated with a not-yet-grouped document have a common group definition and a different between the registration date of the document of interest and the registration date of the not-yet-grouped document is less than or equal to a threshold, the document management unit 14 determines that the document of interest and the not-yet-grouped document are to be grouped, that is, are included in a document group based on the common group definition. Otherwise, the document management unit 14 determines that the document of interest and the not-yet-grouped document are not to be grouped.

Figure 13:
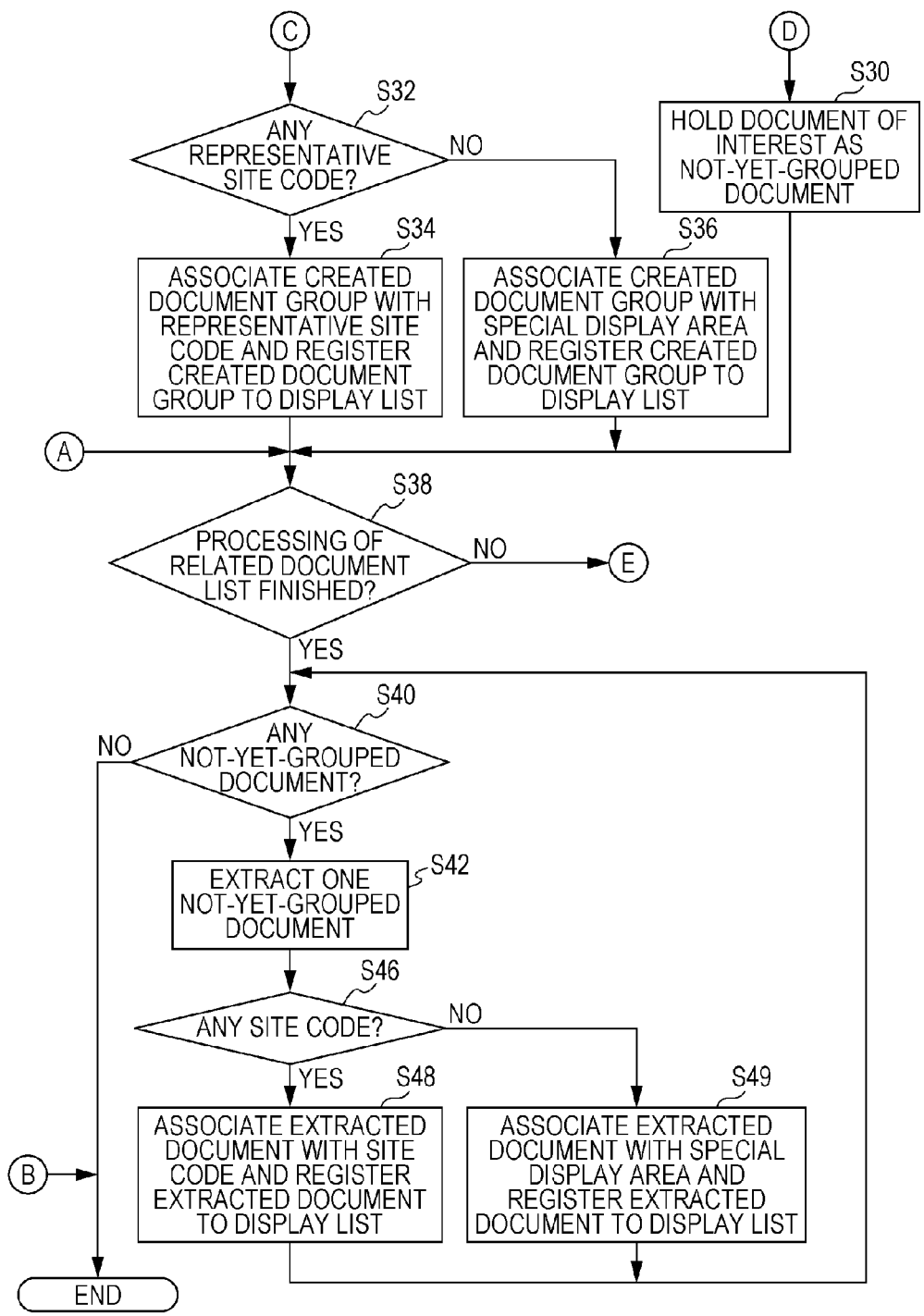
FIG. 13 illustrates the example of the procedure of the search and grouping of search results performed by the document management unit.

Upon the document management unit 14 determining that the document of interest and the not-yet-grouped document are not to be grouped in S26, the process proceeds to S30 of FIG. 13, in which the document management unit 14 holds the document of interest as a not-yet-grouped document. The process then proceeds to S38 of FIG. 13, in which the document management unit 14 determines whether or not processing of all documents contained in the related document list is finished.

Upon determining that the document of interest and the not-yet-grouped document are to be grouped in S26, the document management unit 14 creates a new document group that includes the document of interest and the not-yet-grouped document (S28). Specifically, the document management unit 14 creates a new group ID, and adds the document IDs of the document of interest and the not-yet-grouped document to a document list associated with the group ID. Also, this group ID is associated with the group definition ID of the group definition that is associated with the document of interest and the not-yet-grouped document in common. Then, the document management unit 14 determines whether or not the common group definition contains the representative site code (see FIG. 6) (S32).

If the representative site code is contained, the document management unit 14 associates the document group created in S28 with the representative site code and then registers the document group in the display list (S34).

Here, the display list is a list of display items (document groups or individual documents that do not belong to any document groups) to be displayed on a schema of the search result display screen 100. Each of the display items contained in the display list is displayed as one icon.

In S34, for example, the document management unit 14 associates the group ID of the document group created in S28 with the representative site code and then adds the group ID to the display list.

Upon determining that the group definition associated with the document of interest and the not-yet-grouped document in common does not contain the representative site code in S32, the document management unit 14 associates the document group created in S28 with a code specifying the special display area 135 (see FIG. 8) where documents that are not associated with any sites are arranged, and then registers the document group in the display list (S36).

The process proceeds to S38 from S34 or S36, and the document management unit 14 determines whether or not processing of all documents contained in the related document list is finished.

If the determination result obtained in S38 is negative (NO), that is, if a not-yet-processed document is left in the related document list, the process returns to S18 of FIG. 12, in which the document management unit 14 extracts one not-yet-processed document from the related document list and repeats the processing loop of S20 to S38.

If processing of all documents contained in the related document list is finished as a result of repetition of the processing loop, the determination result obtained in S38 becomes positive (YES) and the process proceeds to S40. In S40, the document management unit 14 determines whether or not not-yet-grouped documents are left. If not-yet-grouped documents are left, the document management unit 14 extracts one document from among the not-yet-grouped documents (S42), attempts to acquire the site code associated with the extracted not-yet-grouped document from the medical record document DB 16, and determines whether or not the site code is successfully acquired (S46). If the site code is successfully acquired, the document management unit 14 associates the document ID of the not-yet-grouped document with the acquired site code and then registers the not-yet-grouped document in the display list (S48). On the other hand, if the site code is not successfully acquired, the document management unit 14 associates the document ID of the not-yet-grouped document with the code indicating the special display area 135 and then registers the not-yet-grouped document in the display list (S49). The process returns to S40 after S48 and S49 are performed, and the document management unit 14 determines whether or not not-yet-grouped documents are left. If not-yet-grouped documents are left, the document management unit 14 repeats processing of S42 to S49. If not-yet-grouped documents are no longer left as a result of repetition of this processing (that is, if the determination result obtained in S40 becomes negative), the process ends.

The example of FIG. 12 describes a flow in which grouping is performed in accordance with group definitions for individual types of medical events illustrated in FIG. 6. For example, in the case where documents regarding one symptom used from the first visit to the recovery are collected into one document group, documents having the same consultation identification information may be grouped using the consultation identification information (identification information assigned in common to documents created for one symptom from the first visit to the recovery) of each of the retrieved documents. In this case, a hierarchical group structure in which, for example, a document group for one symptom from the first visit to the recovery further includes a document group for each medical event, such as a chest examination, may be adopted. To construct this structure, for example, after creating the display list in accordance with the procedure illustrated in FIGS. 12 and 13, the document management unit 14 may group individual document groups and individual documents contained in the display list, in accordance with the consultation identification information. Each symptom is associated with a representative site. An icon for a document group for one symptom used from the first visit to the recovery may be arranged at a position of a schema corresponding to the representative site (a symptom that is not associated with any representative sites may be arranged at the special display area 135).

An example of the procedure from a search to creation of a display list has been described above. The document management unit 14 creates the search result display screen 100 by using the created display list in accordance with a procedure illustrated in FIG. 15, for example.

In this procedure, the document management unit 14 first reads out from the schema memory 15 data of a schema specified by the user (S70). For example, a schema to be used by default may be set to the front view of the whole human body. If the user wishes to use another schema (for example, a partial schema of abdomen), the user may specify the schema in the medical record management system 10. Next, the document management unit 14 determines whether or not the display list contains items (document groups or individual documents) that have not yet been arranged on the schema (S72). If such not-yet-arranged items exist, the document management unit 14 extracts one item from among the not-yet-arranged items (S74). Then, based on attribution information of the extracted item, the document management unit 14 determines a manner (the shape and color) in which an icon is displayed to present the item (S76).

For example, the display manner of the icon (for example, the shape of the icon) may be changed depending on whether the item is a document group or an individual document.

In the case where the display manner (for example, the color) of the icon is changed in accordance with the degree of association, the document management unit 14 acquires the degree of association or the search rank of the document group or document (with respect to the reference document) corresponding to the icon, and selects a display manner corresponding to the degree of association or the search rank. The degree of association or the search rank may be expressed through the shape or color of the icon or may be displayed as a value within the icon. The degree of association or the search rank of the document group with respect to the reference document may be determined from the degrees of association or the search ranks of individual documents contained in the document group with respect to the reference document. For example, the average or the maximum value (the highest value) of the degrees of association (or the search ranks) of documents contained in the document group may be used as the degree of association (or the search rank) of the document group.

Also, the display manner of the icon of a document group may be selected in accordance with a corresponding group definition.

Additionally, the display manner of the icon of a document may be selected in accordance with a document attribute, such as the document type.

Alternatively, document groups and individual documents may be distinguished from each other through the shape of the icon, and the color of the icon may be changed in accordance with an attribute (for example, corresponding to which group definition) of each document group and an attribute of each document. Such a combination may be used.

After determining the display manner of the icon in this way, the document management unit 14 arranges the icon at a position of the schema associated with the icon (S78). In the case of the icon of a document group, the document management unit 14 arranges the icon at a position corresponding to the representative site that is defined in the corresponding group definition. In the case of the icon for a document, the document management unit 14 arranges the icon at a position corresponding to the site code contained in the management data of the document. Here, the icon of a document group or document associated with the special display area 135 is arranged at the special display area 135.

The document management unit 14 repeats the above-described processing of S72 to S78 until not-yet-arranged items are no longer contained in the display list. If not-yet-arranged items are no longer contained in the display list, the process ends. In the case where icons for multiple items are superposed with each other at the same position, items having higher degrees of association may be arranged on the foreground side in the superposition order in one example. As a result, at the position where multiple icons are superposed with each other, an icon having the highest degree of association is in the foreground among the icons when the created search result display screen 100 is first displayed. Thus, the icon having the highest degree of association is likely to be selected through a mouse operation or the like.

As a result of the process described above, the search result display screen 100 in which icons of retrieved document groups and documents are displayed on a specified schema is created. Information of the created search result display screen 100 is returned to the terminal 40, which is the search requestor, via the network 30.

The user who operates the terminal 40 visually grasps what kinds of medical procedures have been performed on which parts of the body of a patient of interest by seeing the search result display screen 100, and selectively views a document regarding a site that is possibly related to a current symptom. Also, the search result display screen 100 in which icons of document groups are displayed on a schema displays retrieved documents that are grouped in accordance with medical events or symptoms that have been cured. Thus, an easier-to-see screen is provided compared with the case where many icons for documents are arranged individually.

A case where a search result of related documents that are related to the reference document is displayed on a schema has been described above but this case is merely an example. In addition to this case, document icons and group icons displayed on a schema may be used also in the case where all medical record documents associated with a specified patient are searched and a result of the search is displayed, in the case where medical record documents that satisfy a specified search condition (for example, a condition regarding a keyword used in a search based on document content or a document attribute) are searched for from among medical record documents associated with a specified patient and a result of the search is displayed, or the like.

In the above-described example, only medical record documents associated with a specified patient are set as a range to be searched in terms of information security. However, in the case where a symptom of a patient of interest is possibly related to an inherited factor, medical record documents associated with relatives related to the patient by blood (genetically) may be exceptionally included in the range to be searched. The range of relatives (within what degree) whose medical record documents are included in the range to be searched may be set in advance.

In one example for making a search operation regarding such a genetic symptom efficient, the reference document is analyzed in S10 of the procedure of FIG. 12 to determine whether or not the reference document is related to a symptom for which an inherited factor is taken into account. In this determination, for example, whether or not document content of the reference document contains pre-registered keywords regarding symptoms for which an inherited factor is taken into account. If such keywords are contained, it is determined that the reference document is related to a symptom for which an inherited factor is taken into account. Instead of the determination simply based on existence or absence of such keywords, it may be automatically determined whether or not the reference document is related to a symptom for which an inherited factor is taken into account by using a natural language interpretation technology.

The medical record management system 10 described above may be implemented by causing a general-purpose computer to execute a program representing a process performed by each functional module described above, for example. Here, the computer has, for example, as hardware, a circuit configuration in which a microprocessor, such as a central processing unit (CPU), a memory (primary storage) such as a random access memory (RAM) and a read only memory (ROM), a hard disk drive (HDD) controller for controlling an HDD, various input/output (I/O) interfaces, a network interface for performing control to establish a connection to a network, such as a local area network, and so forth are connected to each other via a bus. The bus may also be connected to, for example via the I/O interfaces, a disc drive for performing reading from and/or writing to a portable disc recording medium, such as Compact Disc (CD) or a Digital Versatile Disc (DVD); a memory reader/writer for performing reading from and/or writing to a portable nonvolatile recording media based on various standards, such as a flash memory; and so forth. A program in which processing contents of each functional module described above are written is stored in a fixed storage device, such as an HDD, via a recording medium, such as a CD or DVD, or via a communication line, such as a network, and is installed into the computer. The program stored in the fixed storage device is loaded into the RAM and executed by the microprocessor, such as the CPU, whereby the functional modules described above are implemented. Also, the above-described components of the medical record management system 10 may be implemented in a distributed manner by using multiple computers that are able to communicate with each other via a network. The distributed components may communicate with each other via the network, whereby the functions of the medical record management system 10 may be implemented.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A non-transitory computer readable medium storing a program causing a computer to execute a process, the process comprising:
    searching a document memory, the document memory storing electronic documents of medical records of patients in association with document types of the electronic documents, for electronic documents associated with a patient specified by a user from among the patients;
    referring to group definition information that defines document groups and grouping the electronic documents obtained in the searching so as to create the document groups; and
    generating data of a search result display screen in which an icon associated with a corresponding one of the document groups created as a result of the grouping is arranged at a position of a schema, the position corresponding to a site of a human body associated with the document group,
    wherein in the generating,
    in the case where the document groups created as a result of the grouping include two or more document groups associated with the same site of the human body, an image of a schema in which two or more icons respectively associated with the two or more document groups associated with the same site are displayed so as to be superposed with each other at a position of the schema corresponding to the same site is generated and is displayed on the search result display screen, and
    upon a predetermined operation being accepted from the user in a state where a first icon among the two or more icons displayed so as to be superposed with each other at the same position is selected, the selected icon is switched from the first icon to a second icon among the two or more icons.

2. The non-transitory computer readable medium according to claim 1,
    wherein in the generating, upon an icon associated with a document group among the document groups being selected on the search result display screen based on the data, a list of electronic documents contained in the document group associated with the selected icon is created and is displayed on the search result display screen and the content of an electronic document selected from the list is displayed on the search result display screen.

3. The non-transitory computer readable medium according to claim 1, wherein in the searching,
    an operation performed by the user to specify a reference electronic document that is used as a reference in a search is accepted,
    the content of the reference electronic document is analyzed, and
    in a case where the analyzed content is related to an inherited factor,
        another patient who is related to the specified patient by blood in a predetermined range is identified by referring to information about blood relations among the patients, and
        electronic documents of the specified patient and the other patient who has been identified, among the electronic documents stored in the document memory, are searched for electronic documents related to the reference electronic document.

4. The non-transitory computer readable medium according to claim 1, the process further comprising:
    recording, as a concurrently viewed history, information about another electronic document that has been viewed by the user together with a certain electronic document,
    wherein in the searching
        an operation performed by the user to specify a reference electronic document that is used as a reference in a search is accepted, and
        electronic documents associated with the specified patient are searched for electronic documents related to the reference electronic document, in accordance with a degree of association between the content of each electronic document and the content of the reference electronic document and information about the number of times the electronic document has been viewed together with the reference electronic document.

5. A medical record search apparatus comprising:
a search unit, configured by a processor, that searches a document memory, the document memory storing electronic documents of medical records of patients in association with document types of the electronic documents, for electronic documents associated with a patient specified by a user from among the patients;
a grouping unit, configured by a processor, that refers to group definition information which defines document groups and that groups the electronic documents obtained by the search unit so as to create the document groups; and
a generation unit, configured by a processor, that generates data of a search result display screen in which an icon associated with a corresponding one of the document groups created as a result of the grouping performed by the grouping unit is arranged at a position of a schema, the position corresponding to a site of a human body associated with the document group,
wherein in the case where the document groups created as a result of the grouping include two or more document groups associated with the same site of the human body, an image of a schema in which two or more icons respectively associated with the two or more document groups associated with the same site are displayed so as to be superposed with each other at a position of the schema corresponding to the same site is generated and is displayed on the search result display screen, and
upon a predetermined operation being accepted from the user in a state where a first icon among the two or more icons displayed so as to be superposed with each other at the same position is selected, the selected icon is switched from the first icon to a second icon among the two or more icons.

6. A medical record search method comprising:
searching a document memory, the document memory storing electronic documents of medical records of patients in association with document types of the electronic documents, for electronic documents associated with a patient specified by a user from among the patients;
referring to group definition information that defines document groups and grouping the electronic documents obtained in the searching so as to create the document groups; and
generating data of a search result display screen in which an icon associated with a corresponding one of the document groups created as a result of the grouping is arranged at a position of a schema, the position corresponding to a site of a human body associated with the document group,
wherein in the generating,
in the case where the document groups created as a result of the grouping include two or more document groups associated with the same site of the human body, an image of a schema in which two or more icons respectively associated with the two or more document groups associated with the same site are displayed so as to be superposed with each other at a position of the schema corresponding to the same site is generated and is displayed on the search result display screen, and
upon a predetermined operation being accepted from the user in a state where a first icon among the two or more icons displayed so as to be superposed with each other at the same position is selected, the selected icon is switched from the first icon to a second icon among the two or more icons.

* * * * *